United States Patent
Hennig et al.

(10) Patent No.: US 11,335,464 B2
(45) Date of Patent: May 17, 2022

(54) INTEGRATED PRECISION MEDICINE BY COMBINING QUANTITATIVE IMAGING TECHNIQUES WITH QUANTITATIVE GENOMICS FOR IMPROVED DECISION MAKING

(71) Applicant: Siemens Medical Solutions USA, Inc., Malvern, PA (US)

(72) Inventors: Guido Hennig, Cologne (DE); Carl Freiherr Von Gall, West Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 417 days.

(21) Appl. No.: 16/245,626

(22) Filed: Jan. 11, 2019

(65) Prior Publication Data
US 2019/0221314 A1 Jul. 18, 2019

Related U.S. Application Data

(60) Provisional application No. 62/616,449, filed on Jan. 12, 2018.

(51) Int. Cl.
| | |
|---|---|
| *G16H 50/30* | (2018.01) |
| *G16H 10/40* | (2018.01) |
| *G16H 30/40* | (2018.01) |
| *G16H 50/20* | (2018.01) |
| *A61B 5/055* | (2006.01) |
| *A61B 6/03* | (2006.01) |
| *G06T 7/00* | (2017.01) |
| *A61B 5/00* | (2006.01) |
| *A61K 49/00* | (2006.01) |
| *G16H 10/60* | (2018.01) |
| *A61B 6/00* | (2006.01) |

(52) U.S. Cl.
CPC ............ *G16H 50/30* (2018.01); *A61B 5/055* (2013.01); *A61B 5/7275* (2013.01); *A61B 6/037* (2013.01); *A61K 49/00* (2013.01); *G06T 7/0012* (2013.01); *G16H 10/40* (2018.01); *G16H 30/40* (2018.01); *G16H 50/20* (2018.01); *A61B 6/5205* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| 9,551,034 B2* | 1/2017 | Cowens | ................. | G16H 50/20 |
| 10,179,936 B2* | 1/2019 | Shak | .................... | C12Q 1/6886 |
| 10,340,031 B2* | 7/2019 | Bagaev | ..................... | G16B 5/00 |
| 2011/0046979 A1* | 2/2011 | Tulipano | ............... | G16H 50/20 |
| | | | | 705/2 |
| 2013/0268547 A1* | 10/2013 | Boroczky | .............. | G16H 50/70 |
| | | | | 707/758 |
| 2013/0315381 A1* | 11/2013 | Dong | ..................... | A61B 6/035 |
| | | | | 378/209 |
| 2015/0097868 A1* | 4/2015 | Banerjee | ................ | G16H 30/20 |
| | | | | 345/634 |
| 2016/0237506 A1* | 8/2016 | Pritzker | ............... | C12Q 1/6886 |
| 2018/0225424 A1* | 8/2018 | Kaditz | .................... | G16H 50/20 |
| 2019/0304000 A1* | 10/2019 | Simpson | .............. | G01N 33/492 |

OTHER PUBLICATIONS

Bartusik, D. "19F applications in drug development and imaging—a review". Biomedicine & Pharmacotherapy. vol. 68, Issue 6, Jul. 2014, pp. 813-817 (Year: 2014).*
Hamberg, Leena M., et al. "The dose uptake ratio as an index of glucose metabolism: useful parameter or oversimplification?." Journal of Nuclear Medicine 35.8 (1994): 1308.
Gerlinger, Marco, et al. "Genomic architecture and evolution of clear cell renal cell carcinomas defined by multiregion sequencing." Nature genetics 46.3 (2014): 225.
Bettegowda, Chetan, et al. "Detection of circulating tumor DNA in early-and late-stage human malignancies." Science translational medicine 6.224 (2014): 224ra24-224ra24.
Thompson, Jeffrey C., et al. "Detection of therapeutically targetable driver and resistance mutations in lung cancer patients by next generation sequencing of cell-free circulating tumor DNA." Clinical Cancer Research (2016): clincanres-1231.
Diaz Jr, Luis A., and Alberto Bardelli. "Liquid biopsies: genotyping circulating tumor DNA." Journal of clinical oncology 32.6 (2014): 579.

* cited by examiner

*Primary Examiner* — Robert A Sorey

(57) ABSTRACT

Disclosed herein is a combined multi-modality biomarker method for identification and treatment of a disease comprising performing quantitative and/or semi-quantitative molecular imaging on a patient; where the semi-quantitative imaging includes a cut-off; measuring a first plurality of parameters from the quantitative and/or semi-quantitative molecular imaging; simultaneously or sequentially performing a liquid biopsy on the patient; measuring a second plurality of quantitative and/or semi-quantitative molecular parameters from the liquid biopsy; developing an algorithm that combines one or more of the first plurality of parameters and one or more of the second plurality of parameters; where the algorithm is operative to identify a disease and/or predict a course of treatment and/or monitoring the patient; and treating the patient with the course of treatment generated by the algorithm.

10 Claims, No Drawings

INTEGRATED PRECISION MEDICINE BY COMBINING QUANTITATIVE IMAGING TECHNIQUES WITH QUANTITATIVE GENOMICS FOR IMPROVED DECISION MAKING

CROSS-REFERENCE TO RELATED APPLICATIONS

This application claims priority to U.S. Provisional Application No. 62/616,449 filed on Jan. 12, 2018, the entire contents of which are incorporated herein in their entirety by reference.

BACKGROUND

In the practice of modern healthcare, disease identification and diagnosis, treatment planning, treatment monitoring, and the like is being personalized. Precision is desirable in the delivery of personalized health care. A prerequisite to improved personalized medicine is to understand (measure) the specific, functional properties of the disease, which are often determined by and dependent upon the genetic and molecular properties of the pathologic tissue/cells in the patient. These genetic and molecular properties determine the pathologic behavior of a disease. By understanding how genetic and molecular properties influence the transmission and progression of a particular disease in a particular patient, a metabolic pathway that has been directly affected by gene and protein expression or alternatively, can influence and change both gene and protein expression may be determined, thus providing a route for treating the disease. For example in oncology, the properties of a tumor are not only related to the traditional morphology/histology but have been found to be linked to the specific molecular profile (genotype) with certain driver mutations predicting a response to latest and innovative drug treatments.

As personalized and precision medicine are expected to increase the per patient costs in the initial treatment phase, a key driver of implementation (of these types of treatments) is to improve the accuracy of the designed course of personalized treatment, thereby reducing costs to the healthcare provider by making unnecessary, treatments that might prove to be ineffective. In addition, the clinical accuracy (sensitivity and specificity) to avoid both false negative and false positive results needs to be improved to make healthcare more efficient and reduce overall costs.

SUMMARY

Disclosed herein is a combined multi-modality biomarker method for identification and treatment of a disease comprising performing quantitative and/or semi-quantitative molecular imaging on a patient; where the semi-quantitative imaging includes a cut-off; measuring a first plurality of parameters from the quantitative and/or semi-quantitative molecular imaging; simultaneously or sequentially performing a liquid biopsy on the patient; measuring a second plurality of quantitative and/or semi-quantitative molecular parameters from the liquid biopsy; developing an algorithm that combines one or more of the first plurality of parameters and one or more of the second plurality of parameters; where the algorithm is operative to identify a disease and/or predict a course of treatment and/or monitoring the patient; and treating the patient with the course of treatment generated by the algorithm.

Disclosed herein too is a system comprising a microprocessor; where the microprocessor is operative to collect and store a first plurality of parameters obtained from quantitative or semi-quantitative molecular imaging conducted on a patient; collect and store a second plurality of parameters obtained from a liquid biopsy conducted on the patient; and generate an algorithm that uses one or more parameters from the first plurality of parameters and one or more parameters from the second plurality of parameters; where the algorithm provides a course of therapy to the patient; and wherein the patient performs the course of treatment.

DETAILED DESCRIPTION

Disclosed herein is a combinatorial approach that links functional and quantitative modalities (or semi-quantitative modalities) such as imaging and molecular diagnostics into one combined multi-modality biomarker approach. This combined multi-modal biomarker approach informs decision making and facilitates the development of a platform from which correlations between the results obtained from imaging and those obtained from molecular diagnostics can be identified. This platform can also facilitate the identification of mutual synergistic benefits between functional and quantitative modalities for developing personalized treatments for patients. This method is very useful in the early detection of cancers.

Liquid biopsies can be used for detecting the functional molecular properties of a tumor or a disease by comprehensive and quantitative molecular analysis of the patient's fluid sample (mostly blood plasma) from circulating-free tumor deoxyribonucleic acid (ctDNA) or circulating-free tumor ribonucleic acid (ctRNA), or both (circulating-free tumor total nucleic acids, ctNA). Liquid biopsies can include analysis of any body fluids (e.g., blood, urine, saliva, tears, stools, ear-wax, sweat, breast milk, and the like) or solid cells (e.g., circulating tumor cells) from these liquid biopsies such as breast, esophagus, intestine, and the like. In other words, the fluids obtained for examination can be obtained by non-invasive techniques or low- or minimally-invasive techniques (with respect to a fully invasive tissue biopsy). This liquid biopsy approach has the advantage of capturing the complex molecular heterogeneity of a disease or a tumor and its metastasis from one low cost and relatively painless sample especially from blood ("molecular whole body scan" from blood). The results may be used for identifying a disease and/or therapy decision making. This method may be used in lieu of an invasive tissue biopsy.

The analytical and clinical specificity of a cancer or disease-specific mutation in a liquid biopsy has been shown to be excellent, such as, for example, in targeted cancer therapy decision making (close to 100% vs tissue sample). However, one of the big challenges of ctDNA mutation detection is the analytical and clinical sensitivity from reasonable amounts of blood due to limited shedding (and rapid degradation) of tumor DNA into the blood (down to very low concentrations in plasma to a few nanograms per milliliter (ng/ml), if at all) especially in the early stages of the disease for certain histological cancer types. Therefore the diagnostic power as a stand-alone tool is limited, especially in certain applications, such as screening and staging.

Changes in radioactive tracer distribution due to metabolic changes in a certain tissue are also useful in identifying diseases by their functional changes rather than because of morphological alterations. However, in spite of the validity of the widely used approved tracer 2-deoxy-2-[fluorine-18] fluoro-D-glucose [FDG], improvements in accuracy, in particular, in specificity are desirable. Driven by mimicking glucose metabolism up to a certain level, FDG's lack of specificity can be overcome by dynamic positron emission tomography (PET) scans and several different kinetic modelling approaches.

However, technical as well operational barriers prevent the use of dynamic PET/(computerized tomography) CT scans. A typical scan typically takes 60 to 90 minutes after injection of the radioactive trace into the body. The length of scan time together with the lack of automated approaches for the different steps in dynamic, kinetic PET technology (in order to overcome the axial field of view limitations) are drawbacks which hitherto have prevented the prolific use of these techniques. Each of the aforementioned techniques and approaches have contributed to a better understanding of certain diseases which has led to further support for the development of precision personal medicine, but a) the technical feasibility in clinical routine for different disease settings and different stages of the disease cycle are limited or even missing; and b) each of these approaches has limitations in both analytical and clinical accuracy (sensitivity and/or specificity).

As noted above, the inventive combinatorial approach detailed herein links functional and quantitative modalities such as imaging and molecular diagnostics into one combined multi-modality biomarker approach. This new approach combines quantitative or semi-quantitative molecular imaging (e.g., dynamic positron emission tomography) with molecular liquid results (e.g., ctDNA). The semi-quantitative molecular imaging typically includes a cut-off.

The quantitative or semi-quantitative molecular imaging provides results in the form a first set of parameters, while the molecular analysis include liquid biopsy and provides results in the form of a second set of parameters. The molecular liquid biopsy results and the imaging may be conducted sequentially or simultaneously. In an embodiment, the molecular liquid results may be obtained first followed by the quantitative molecular imaging. In another embodiment, the quantitative molecular imaging may be obtained first followed by the molecular liquid results. The results of both of these approaches are then developed into an algorithm for the particular patient.

Data obtained from one approach (imaging) may be used to modify data obtained in the other approach (liquid biopsy) and vice versa. The algorithm may include one or more of the first set of parameters and one or more of the second set of parameters and may be a predictive algorithm. In a preferred embodiment, the molecular liquid results may be obtained first followed by the quantitative molecular imaging.

This predictive algorithm improves clinical sensitivity and specificity, which improves the accuracy of diagnosis and/or therapy delivery. It is believed that this method will result in fewer false positives and false negatives. This allows more accurate detection of disease population in screening scenarios and also reduces the risk of an inaccurate course of treatment (e.g., under-treatment or over-treatment), which increases economic efficiency and reduces costs.

The quantitative molecular imaging includes quantitative functional multi-parametric molecular imaging. Molecular imaging includes x-ray computed tomography (CT), magnetic resonance imaging (MRI), functional magnetic resonance imaging (MRI), magnetic resonance fingerprinting, ultrasound and single-photon emission computed tomography (SPECT), positron emission tomography, or a combination thereof. Multi-parametric x-ray computed tomography (CT), magnetic resonance imaging (MRI), functional magnetic resonance imaging (MRI), ultrasound and single-photon emission computed tomography (SPECT), positron emission tomography, or a combination thereof is preferred. Multi-parametric positron emission tomography and multi-parametric magnetic resonance imaging are preferred.

In an embodiment, multi-parametric positron emission tomography is preferred. The quantitative functional multi-parametric molecular imaging includes dynamic positron emission tomography, which includes automated multi-parametric positron emission tomography results. Dynamic positron emission tomography (PET) imaging provides useful quantitative information on physiological and biochemical processes. Associative parametric imaging can be achieved by fitting the time activity curves (TACs) at each voxel with a linear or nonlinear kinetic model. Direct reconstruction methods enable accurate compensation of noise propagation from the projection data to the kinetic fitting process by combining kinetic modeling and dynamic image reconstruction into a unitary formula.

In an embodiment, reconstruction may not be performed and the data may only be subjected to a transformation (e.g., from Cartesian coordinates to polar coordinates and vice-versa). In yet another embodiment, the data may be subjected to both a transformation and reconstruction (not in the specific order as stated here).

Reconstruction can include direct reconstruction, indirect reconstruction, iterative reconstruction, or a combination thereof.

Direct reconstruction methods usually utilize knowledge of the input function, that is, the TAC of tracer concentration in arterial blood. As regards indirect reconstruction methods, dynamic image reconstruction and kinetic analysis are conducted separately. In an embodiment, an image-derived input function method or a reference region method may be employed for indirect reconstruction.

To achieve high-quality dynamic PET images, several strategies may be used, namely, maximum a posteriori (MAP) image reconstruction and image restoration based post-processing. MAP image reconstruction with significant noise suppression is performed by incorporating different prior models, such as the spatial quadratic smoothing prior, sophisticated edge-preserving priors, anatomical priors, and kinetics-based priors.

3D (3-dimensional) OSEM is an iterative method that may be used for data reconstruction. 3D OSEM provides superior image quality over existing 2D reconstruction techniques by producing sharper, higher contrast images. This technique provides such a significant improvement in image quality enabling clinicians to reduce acquisition times or patient dose.

In an embodiment, image post-processing may be conducted without the use of a filter or alternatively, with the use of spatial filters. Image post-processing through spatial filtering may be conducted to reduce the noise of individual PET image frames. Gaussian filters and/or bilateral filters (BF), are used to reduce noise and resolution preservation. These spatial filters reduce the noise of individual image frames without considering the kinetic information contained within entire dynamic images. A recently increasing interest in dynamic PET image filtering is the use of the temporal information from dynamic PET data. In a preferred embodiment, image post-processing is conducted without the use of a filter and "all pass data" for dynamic data and kinetic modelling is used. All pass data means data that is used without using a filter.

The quantitative functional multi-parametric molecular imaging includes dynamic positron emission tomography, which includes automated multi-parametric positron emission tomography results [e.g., in SUV (Standardized Uptake Value), MTV (Metabolic Tumor Volume), FDG TLG (Total Lesion Glycolysis), Ki, VB [Patlak, Logan], K1, k2, k3, k4, and the like. The multi-parametric positron emission tomography results obtained from the quantitative functional multi-parametric molecular imaging are referred to as a first plurality of parameters. One or more of these parameters may be used in the algorithm.

Standardized uptake value (SUV) of primary tumors at FDG PET is valuable as a prognostic indicator of survival in patients with non-small cell lung cancer (NSCLC). The standard uptake value (SUV) is a simple way of determining activity in PET imaging, most commonly used in fluorodeoxyglucose (FDG) imaging. It is also known as the dose uptake ratio (DUR).

FDG PET may be used to measure tumor burden in relation to the degree of malignancy. High tumor-to-background intensity ratios at FDG PET enable computer-assisted measurement of total body metabolic tumor volume (MTV) or total lesion glycolysis (TLG). Metabolic tumor volume (MTV) is defined as the volume of hypermetabolic tissue within the region of the gross tumor with a standardized uptake value greater than a defined threshold. Total lesion glycolysis (TLG) is the product of mean SUV and MTV.

As noted above, the dynamics of PET radiotracer uptake can provide valuable information for staging of cancer and treatment monitoring. The uptake and washout of the tracer is typically represented using a multi-compartment model with parameters that characterize the rate of exchange between compartments. These parameters are typically estimated either indirectly from reconstructed images, or directly from either sinograms or list mode data. The compartment models and their parameter estimators are nonlinear, leading to a complex non-convex optimization problem, resulting in possibly suboptimal solutions at high computational cost. In an embodiment, fitting that uses complex advanced and trained algorithms, e.g. SVM (support vector machine), NN (neural networks), and the like may be used.

The Patlak method simplifies the nonlinear problem of estimating the full set of parameters of a three compartment model by considering tracer uptake only during a steady state where changes in concentration are due to irreversible trapping in a single compartment. The slope of the Patlak model is a useful quantitative index that characterizes the net influx rate of the tracer into a region of interest. Compared with full compartment model estimation, Patlak analysis, and the related Logan plot, are used in dynamic PET studies because of the relatively simple calculations used and their resulting robustness. Estimating the Patlak parameters, rather than other static measures such as the standardized uptake value (SUV), may lead to more accurate evaluation of cancer therapy in FDG PET as it enables a differentiation between trapped non-metabolized and metabolized tracer, reflecting specific metabolic steps in the glucose pathway.

Most estimation methods indirectly estimate Patlak parameters from reconstructed images either voxel by voxel, or more typically over some region of interest. In an embodiment, a filtered back projection method may be used to estimate the Patlak parameters directly from projection data. In another embodiment, a Bayesian method may be used to reconstruct the Patlak parametric images directly from sinograms. They also showed that, direct estimation of Patlak parameters from the sinogram can achieve better bias-variance trade off than the indirect approach.

A more sophisticated approach rather than Patlak or Logan approaches are kinetic models, such as the two-compartment modelling, that uses more data points over time than Patlak or Logan but enables the direct calculation of the individual metabolic steps from into the first compartment, e.g. transportation in the intracellular space, the metabolization of the tracer into a status, where it remains trapped, the reversing step and the elimination of the tracer of the intracellular space into the either supporting blood stream or intercellular space.

In the case of FDG, this is in alignment of the Sokoloff model of glucose metabolism provides:

K1: uptake from e.g. the vessel into the intracellular space k3: phosphorylation of Glucose [FDG] by the enzyme Hexokinase k2: de-phosphorylation of Glucose-6-P by the enzyme Dephosphatase k4: elimination [either active or passive] transport of Glucose [FDG] into the e.g. supporting vessel.

Continuous bed motion technology provides the ability to develop and save protocols based on clinical indication so they are easily incorporated into clinical routine—to enable reliable visualization of disease. Continuous bed motion technology (commercially termed FLOWMOTION®) uses a magnetically driven table and new data processing models, resulting in continuous bed motion throughout the entire procedure.

While the description above details the use of the FDG radioactive tracer in the PET imaging, other radiotracers with sensitive, pan-cancer specificity (imaging complement to circulating tumor DNA load) may also be used.

As noted above, the data obtained from dynamic parametric imaging is combined with a functional molecular genotype or profile or information obtained from a liquid biopsy. A liquid biopsy, also known as fluid biopsy or fluid phase biopsy, is the sampling and molecular analysis of either the non-solid circulating cellular-free nucleic acid fraction, primarily the plasma fraction from whole blood or a circulating tumor cell fraction.

This method may also be non-invasive or minimally invasive (e.g. blood draw). Urine or other body fluids may also be sampled either separately or in conjunction with blood. This technique is mainly used as a diagnostic and monitoring tool for diseases such as cancer, with the added benefit of being largely non-invasive. The molecular data or results or information obtained from the liquid biopsy are referred to as the second (or first as above) plurality of quantifiable or scorable parameters.

Molecular information from liquid biopsies can be obtained from analysis of different fractions of the patient liquid sample including the circulating tumor cell fraction and especially from circulating cellular-free nucleic acid fraction which can comprise an exosomal nucleic acid fraction, circulating-free DNA, total circulating-free tumor DNA (ctDNA), total circulating-free RNA (cfRNA), total circulating-free tumor RNA (ctRNA), total circulating-free nucleic acid (cfNA) and/or total circulating-free tumor nucleic acid (ctNA).

The type of molecular information reported from any of the above liquid biopsy fractions includes (but is not limited to) absolute or relative amounts of circulating-free DNA, circulating-free tumor DNA (ctDNA), circulating-free RNA (cfRNA), circulating-free tumor RNA (ctRNA), circulating-free nucleic acid (cfNA) or circulating-free tumor nucleic acid (ctNA), mutational load/burden (amount of nucleic acid harboring mutations), FGA (fraction of genome altered), MSI (microsatellite instability), fraction/percentage of MRD (mismatch repair deficiency), methylated tumor DNA fraction, nucleosomal organization of circulating free or tumor DNA or a combination thereof.

Fraction (or percentage) of Genome Altered (FGA) is the percentage of a genome that has been affected by copy number gains or losses. Total mutations refers to the number of mutations that are found in the tumor genome. Both attributes are useful for genetic researchers as they provide more in-depth information on the genomic make-up of the tumors. The attributes are also useful for finding correlations with specific alterations or clinical attributes, such as survival or tumor stage.

Microsatellite instability (MSI) is the condition of genetic hypermutability (predisposition to mutation) that results from impaired DNA mismatch repair (MMR). Microsatellite sequences (MS) are repeated sequences of short stretches of DNA all over the genome. Microsatellite stability (MSS) means MS are the same in each cell of an individual, whereas microsatellite instability (MSI) means MS differs in normal and cancer cells of an individual. The presence of MSI represents phenotypic evidence that MMR is not functioning normally. MSI can be scored semi-quantitatively as being high, medium, or low.

DNA mismatch repair (MMR) is a system for recognizing and repairing erroneous insertion, deletion, and mis-incorporation of bases that can arise during DNA replication and recombination, as well as in repairing some forms of DNA damage. Mismatch repair is strand-specific. During DNA synthesis, the newly synthesized (daughter) strand will commonly include errors. In order to begin repair, the mismatch repair machinery distinguishes the newly synthesized strand from the template (parental). Fraction or percentage of DNA mismatch repair can be scored semi-quantitatively as being high, medium, low or negative.

Contamination of normal cells is almost always present in tumor samples and affects their molecular analyses. DNA methylation, a stable epigenetic modification, is cell type-dependent, and different between cancer and normal cells and is also tissue of origin specific (important to correlate a given mutation in liquid biopsy with location of primary tumor or metastasis from imaging). Contamination of normal cells, such as normal epithelial cells, fibroblasts, and peripheral leukocytes, is almost always present in tumor samples. Such contamination influences the results of cancer genome analyses and RNA expression analysis. If the fraction of cancer cells in a tumor DNA sample can be readily assessed, a more accurate analysis can be conducted by excluding samples with extremely low tumor cell content, and by normalizing the raw data based upon the fraction of cancer cells. Traditionally, a fraction of cancer cells in a tumor sample can be assessed by pathological analysis using neighboring sections.

Tumor mutational load or mutation burden is a measure of the number of mutations within a tumor genome, defined as the total number of mutations per coding area of a tumor genome. There is large variability in mutation burden within tumor types, ranging from just a few to 1000s of mutations. Lower grade and pediatric malignancies tend to have the lowest mutation burden, while epithelial cancers, associated with environmental DNA damage, are most highly mutated. Tumor mutational load or mutation burden is normally expressed as number of mutations/megabase of DNA or RNA sequence.

For example, in patients with non-small cell lung cancer (NSCLC), tumors of never-smokers have few somatic mutations compared with tumors of smokers which may have 10-fold more. Melanomas also have very high mutational burdens (0.5 to >100 mutations per megabase [Mb]) as compared with other solid tumors and important studies have shown that these somatic mutations can give rise to neoepitopes and that these may serve as neoantigens.

Measuring mutational load can act as a proxy for determining the number of neoantigens per tumor, and may offer a potential addition to the current targeted therapy landscape that can be combined with protein and gene expression markers to help inform physicians to maximize the benefits of immunotherapy.

Nucleosomal organization of circulating free or tumor DNA is due to non-random, disease specific or pathogenic or tissue specific fragmentation which can be measured by paired-end sequencing and statistical analysis and expressed quantitatively by number of preferred end or breakpoint fragments.

In one manner of using the combined multi-modality biomarker approach, a patient is first subjected to multi-parametric imaging using one of the techniques listed above. One or more first parameters such as the standardized uptake value, metabolic tumor volume, total lesion glycolysis, Ki, VB [Patlak], K1, k2, k3, k4, and the like may be measured. The imaging may include a complete or partial body scan using continuous bed motion technology.

Simultaneously or sequentially, the patient is subjected to liquid biopsy and one or more second parameters such as total circulating free DNA (and/or RNA or NA), total circulating tumor DNA (and/or RNA or NA), mutational load/burden, fraction of genome altered, microsatellite instability, mismatch repair deficiency, methylated tumor DNA fraction, nucleosomal organization of circulating free or tumor DNA and the like may be measured. These measurements and the results obtained may be analyzed and used in the development of a combined algorithm.

The combined algorithm combines one or more parameters (i.e., one or more of the first plurality of parameters and one or more of the second plurality of parameters) obtained from both approaches and encompasses the combined multi-modality biomarker approach. This algorithm may be validated by further testing on the patient using both imaging and molecular diagnostics. In other words, the validation may be conducted using a combined multi-modality biomarker approach. The algorithms derived from both functional modalities is predictive and facilitates improved decision making and patient outcomes including disease identification and diagnosis, treatment planning as well as treatment monitoring with assessing response, prediction and detection of recurrence of a disease.

The benefit of these dual approaches is in the parallel visualization of the two modalities to faster and more conveniently identify additional information in one read. The method disclosed herein extends beyond the combinatory approach of visual combination of different imaging modalities.

This method operates on two or more approaches that include A) combining specific imaging techniques that have for example, a high specificity [modality 1] and high sensitivity [modality 2], visualizing them in a weighted way, so that the reader can identify regions with probable relevant changes first, due to the high sensitivity and high specificity. B) going beyond the combinatorial approach of combining specific imaging techniques and combining the optimal metabolic/functional imaging technique for the purpose, e.g., multi-parametric PET, with the highest sensitivity and combining it with the best laboratory test, e.g. liquid biopsy.

The second approach ((B) above) has the non-obvious criteria in that two modalities are combined that usually are not visualized in the same matrix or way. In this method, the non-imaging information is linked to a weight associated with the imaging information. By applying an algorithm, such as, for example, one that employs artificial information, the practitioner can review only relevant findings based upon this new combinatorial visualization approach.

The disclosed method uses imaging and/or non-imaging information and visualizes it in a combinatorial approach. This method uses the extra information [either of imaging or non-imaging] and combines them into a new color/overlay map to weight the new multi-parametric image [derived from non-imaging and imaging] that is then used to deliver a new more precise course of therapy (treatment). In other words, information derived from the imaging or from the liquid biopsy, is used to create one or more weighting function for the algorithm that prescribes a more precise course of treatment.

In an embodiment, information received from the first plurality of parameters is used to modify information received from the second plurality of parameters. In another embodiment, information received from the second plurality of parameters is used to modify information received from the first plurality of parameters. In yet another embodiment, information received from the first plurality of parameters and/or the second plurality of parameters is used to create a modified weighted data set that is used for improved decision making. This improved decision making results in a course of treatment that would not be given to the patient if information received from the first plurality of parameters or from the second plurality of parameters was not available.

The plurality of parameters implies 2 or more parameters. For example, the first plurality of parameters can include 2 or more parameters, 3 or more parameters, 4 or more parameters, 5 or more parameters, and so on. For example, the second plurality of parameters can include 2 or more parameters, 3 or more parameters, 4 or more parameters, 5 or more parameters, and so on. Any combination of the first plurality of parameters and/or second plurality of parameters can be used to create a modified weighted data set that is used for improved decision making.

The treatment that is arrived from the algorithm may include determination and delivery of therapeutic treatment including dosages of medicine to the patient, chemotherapy, and the like. The delivery of medicine may be performed by the patient or by a nursing assistant, doctor, skilled technician, and the like. The combined multi-modality biomarker approach has a number of advantages because it can reduce overall system costs by precise disease identification (with improved clinical validity/accuracy by reducing false negatives and/or false positives) and by providing more precise courses of therapy.

The course of therapy (treatment) can include ruling out and avoiding unnecessary treatments, reducing overtreatment, probabilistic analysis of the disease(s) that the patient may be suffering from, which includes certain diseases and excludes some diseases (e.g., identifying lesions that are cancerous and distinguishing those from ones that are non-cancerous), screening and therapy planning and monitoring, or a combination thereof.

In an embodiment, the method disclosed herein may be effected by a microprocessor. The microprocessor is operative to collect and store a first plurality of parameters obtained from a quantitative molecular imaging conducted on a patient and to collect and store a second plurality of parameters obtained from a liquid biopsy conducted on the patient. The microprocessor can generate an algorithm that uses one or more parameters from the first plurality of parameters and one or more parameters from the second plurality of parameters. The algorithm provides a course of therapy to the patient who performs the course of treatment. The method may be used for screening, diagnosis, staging, treatment planning, decision-making, monitoring, after care, or a combination thereof.

The method, the analysis, the results and calculation performed on the results can be implemented as logic executed in one or more computing devices. A computing device according to the disclosure can include at least one processor and a memory, both of which are in electrical communication with a local interface. To this end, the computing device may comprise, for example, at least one server computer or like device. The local interface may comprise, for example, a data bus with an accompanying address/control bus or other bus structure as can be appreciated.

Stored in the memory are both data and several components that are executable by the processor. In particular, stored in the memory and executable by the processor is an application implementing logic according to mathematical principles as well as potentially other applications. It is understood that there may be other applications that are stored in the memory and are executable by the processors. Where any component discussed herein is implemented in the form of software, any one of a number of programming languages may be employed such as, for example, C, C++, C#, Objective C, Java, Javascript, Perl, PHP, Visual Basic, Python, Ruby, Delphi, Flash, or other programming languages.

A number of software components are stored in the memory and are executable by the processor. In this respect, the term "executable" means a program file that is in a form that can ultimately be run by the processor. Examples of executable programs may be, for example, a compiled program that can be translated into machine code in a format that can be loaded into a random access portion of the memory and run by the processor, source code that may be expressed in proper format such as object code that is capable of being loaded into a random access portion of the memory and executed by the processor, or source code that may be interpreted by another executable program to generate instructions in a random access portion of the memory to be executed by the processor, and the like. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RANI may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although executable logic of an embodiment of the disclosure may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, and the like.

Also, any logic or application according to an embodiment of the disclosure that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The data can be stored on the cloud and can be made accessible to specialists across the world. This will permit remote access of images and laboratory (including molecular) data and testing of patients in remote regions across the world. Storage of data on the cloud can be used to compare behavior or morphology in normal populations versus diseased populations and to aggregate such statistics in mass populations.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A combined multi-modality biomarker method for identification and treatment of a disease comprising:

performing quantitative and/or semi-quantitative molecular imaging on a patient; where the semi-quantitative imaging includes a cut-off;

measuring a first plurality of parameters from the quantitative and/or semi-quantitative molecular imaging; wherein the quantitative molecular imaging includes quantitative functional multi-parametric molecular imaging; wherein the quantitative functional multi-parametric molecular imaging includes x-ray computed tomography, magnetic resonance imaging, functional magnetic resonance imaging, ultrasound and single-photon emission computed tomography, positron emission tomography, or a combination thereof; wherein the first plurality of parameters include standardized uptake value, metabolic tumor volume, total lesion glycolysis, Ki, VB [Patlak, Logan], K1, k2, k3, k4, or a combination thereof;

simultaneously or sequentially performing a liquid biopsy on the patient;

measuring a second plurality of quantitative and/or semi-quantitative molecular parameters from the liquid biopsy; where information received from the first plurality of parameters is used to modify information received from the second plurality of parameters or where information received from the second plurality of parameters is used to modify information received from the first plurality of parameters; wherein the second plurality of parameters includes molecular information from circulating tumor cells, circulating-free DNA, circulating-free RNA, circulating-free nucleic acids, circulating tumor DNA (ctDNA), circulating tumor RNA (ctRNA), circulating tumor nucleic acids (ctNA), mutational load/burden, fraction of genome altered, microsatellite instability, mismatch repair deficiency, methylated tumor DNA fraction, nucleosomal organization/fragmentation of circulating free or tumor DNA;

generating, by a microprocessor, a predictive algorithm that combines one or more of the first plurality of parameters and one or more of the second plurality of parameters; where the algorithm is operative to at least identify a disease and provide a course of treatment; and treating the patient with the course of treatment generated by the algorithm.

2. The method of claim 1, wherein the liquid biopsy is non-invasive and is conducted on a body fluid.

3. The method of claim 2, wherein the body fluid is blood, urine, or a combination thereof.

4. The method of claim 1, wherein the quantitative functional multi-parametric molecular imaging includes the use of a radioactive tracer that comprises fluorine.

5. The method of claim 1, where the method may be used for screening, diagnosis, staging, treatment planning, decision-making, monitoring, after care, or a combination thereof.

6. The method of claim 1, where the quantitative and/or semi-quantitative molecular imaging is performed prior to the liquid biopsy.

7. The method of claim 1, where the liquid biopsy is performed prior to the quantitative and/or semi-quantitative molecular imaging.

8. The method of claim 1, where the course of treatment includes ruling out and avoiding unnecessary treatments, reducing overtreatment, probabilistic analysis of the disease(s) that the patient may be suffering from, screening and therapy planning, monitoring of patient wellness, or a combination thereof.

9. The method of claim 1, where information received from the first plurality of parameters and/or from the second plurality of parameters is used to generate a weighted data set that is used for decision making.

10. The method of claim 1, where the first plurality of parameters is subjected to reconstruction and/or transformation.

* * * * *